United States Patent [19]
d'Orchymont et al.

[11] Patent Number: 5,608,078
[45] Date of Patent: Mar. 4, 1997

[54] PHOSPHONOMETHYLDIPEPTIDES AND PROCESS FOR PREPARATION THEREOF

[75] Inventors: Hugues d'Orchymont; Marc Bigaud, both of Strasbourg, France

[73] Assignee: Merrell Pharmaceuticals Inc., Cincinnati, Ohio

[21] Appl. No.: 501,018

[22] PCT Filed: Feb. 22, 1994

[86] PCT No.: PCT/US94/01716

§ 371 Date: Nov. 13, 1995

§ 102(e) Date: Nov. 13, 1995

[87] PCT Pub. No.: WO94/22908

PCT Pub. Date: Oct. 13, 1994

[30] Foreign Application Priority Data

Mar. 30, 1993 [EP] European Pat. Off. .............. 93400824

[51] Int. Cl.⁶ .................................................. C07D 209/14
[52] U.S. Cl. ......................... 548/414; 548/496; 548/497
[58] Field of Search .................................. 548/496, 497, 548/414

[56] References Cited

U.S. PATENT DOCUMENTS 5,380,921  1/1995  Ishikawa et al. .................... 562/16

FOREIGN PATENT DOCUMENTS 0320118  6/1989  European Pat. Off. ..
0518299  12/1992  European Pat. Off. ..
4041430  2/1992  Japan .
0148277  6/1993  Japan .
9201468  2/1992  WIPO .
9213545  8/1992  WIPO .

OTHER PUBLICATIONS

J. Med. Chem. vol. 36, No. 1, pp. 173–176 (1993) S. R. Bertenshaw et al. "Phosphorus–containing inhibitors of endothelin converting enzyme: Effects of the electronic nature of phosphorus on inhibitor potency".

Biochem. and Biophysical Research Comm. vol. 186, No. 2, pp. 1146–1150 (1992) D. M. Pollock et al. "Rhamnose moiety of phosphoramidon is not required for in vivo inhibition of endothelin converting enzyme".

Chemical Abstracts vol. 119, No. 1, pp. 9174 (1993) Kimura Sadao et al. "Phosphonamides".

J. Med. Chem. vol. 33, No. 1, pp. 263–273 (1990) Z. P. Kortylewicz et al. "Phosphoramidate peptide inhibitors of human skin fibroblast collagenase".

Bioorganic & Medicinal Chemistry Letters vol. 4, No. 10, pp. 1257–1262 (1994) Takahiro Fukami et al. "Aminophosphonate endothelin converting enzyme inhibitors: potency-enhancing and selectivity-improving modifications of phosphoramidon".

*Primary Examiner*—Jacqueline Haley
*Attorney, Agent, or Firm*—Carolyn D. Moon; Craig G. Svoboda

[57] ABSTRACT

Dipeptide compounds and analogs thereof having a phosphonomethyl moiety are disclosed. These compounds inhibit Endothelin Converting Enzyme and are thus useful in treating conditions responsive to inhibition of production of Endothelin.

15 Claims, No Drawings

PHOSPHONOMETHYLDIPEPTIDES AND PROCESS FOR PREPARATION THEREOF

This is a National Stage Application of PCT/US 94/01716 filed Feb. 22, 1994, published as WO 94/22908 on Oct. 13, 1994.

FIELD OF THE INVENTION

This invention generally relates to dipeptides and analogs thereof having a phosphonomethyl moiety, pharmaceutical compositions comprising these compounds, processes for making such compounds, intermediates used in these processes, and methods for inhibiting the production of Endothelin. These compounds inhibit Endothelin Converting Enzyme and are thus useful in treating conditions responsive to inhibition of production of Endothelin.

BACKGROUND OF THE INVENTION

The peptide Big Endothelin, found in endothelium cells, is cleaved by the enzyme Endothelin Converting Enzyme (ECE) to produce the peptide Endothelin. Endothelin is a 21 amino acid vasoconstrictor and is produced by endothelium cells, mesangial, kidney and epithelial cells and by various human cancer cell lines and human macrophages.

Biologically, endothelin has effects on vascular smooth muscle, nonvascular smooth muscle, heart, nervous tissue, kidney and adrenal glands. Endothelin constricts arteries and veins, increases mean arterial blood pressure, decreases cardiac output, increases cardiac contractility in vitro, stimulates mitogenesis in vascular smooth muscle cells in vitro, contracts vascular smooth muscle including guinea pig trachea, human urinary bladder strips and rat uterus in vitro, increases airway resistance in vivo, induces formation of gastric ulcers, stimulates release of atrial natriuretic factor in vitro and in vivo, increases plasma levels of vasopressin, aldosterone and catecholamines, inhibits release of renin in vitro and stimulates release of gonadrotropin in vitro. See, for example, PCT patent application publication No. Wo 92/13545.

Possible indications for use of inhibitors of production of endothelin include treatment of cardiovascular diseases (e.g., myocardial ischemia, congestive heart failure, arrhythmia, unstable angina and hypertension); bronchoconstriction (pulmonary hypertension and asthma); neuronal action disorders (cerebral vasospasm and subarachnoid hemorrhage); endocrine disorders (pre-eclampsia); renal disease (acute/chronic renal failure); vascular disorders (atherosclerosis, Buergers disease, Takayasu's arteritis, Raynaud's phenomenon and complications in diabetes); cancer (especially pulmonary carcinoma; gastric mucosal damage (gastrointestinal disorders); and endotoxic shock and septicemia. See *J. Med. Chem.* 35(9): 1493–1508 (1992); *Neurology* 42:25–31 (1992); and *Drug Development Research* 26:361–387 (1992).

SUMMARY OF THE PRESENT INVENTION

A compound having the formula of:

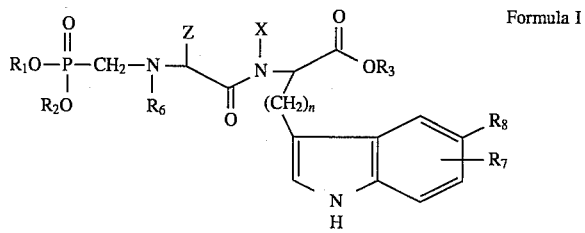

Formula I stereoisomers, hydrates, inner salts or pharmaceutically acceptable salts thereof,
wherein $R_1$ or $R_2$ are each independently a hydrogen, $C_{1-6}$ alkyl, $(CH_2)_m$-aryl, $R_4$—C(O)O—CH($R_5$)— or nothing when the inner salt is formed, provided that when one of $R_1$ or $R_2$ is a hydrogen, $C_{1-6}$ alkyl, or $(CH_2)_m$-aryl, then the other is hydrogen or nothing when the inner salt is formed;

$R_3$ is hydrogen, $C_{1-6}$ alkyl, $(CH_2)_m$-cycloalkyl or $(CH_2)_m$-aryl;

$R_4$ is $C_{1-10}$ alkyl, $(CH_2)_m$-cycloalkyl or $(CH_2)_m$-aryl;

$R_5$ is $C_{1-6}$ alkyl, $(CH_2)_m$-cycloalkyl or hydrogen;

$R_6$ is H, or $H_2$ when one of $R_1$ or $R_2$ is nothing thus forming the inner salt;

$R_7$ is $CH_3$ or H;

$R_8$ is H, Br, $CH_3$, or $OCH_3$, provided that one of $R_7$ or $R_8$ are H;

Z is $(CH_2)_m$-aryl or $C_{1-12}$ alkyl;

X is hydrogen or $C_{1-6}$ alkyl;

each m is independently 0, 1, 2 or 3; and n is 1, 2 or 3, compositions comprising Formula I and using the compounds of Formula I for treatment of conditions improved by the inhibition of Endothelin Converting Enzyme.

DETAILED DESCRIPTION OF THE PRESENT INVENTION

As used herein, certain terms have specific meanings such as those that follow.

"Cycloalkyl" means a saturated carbon atom ring having 3 to 8 carbon atoms including, but not limited to, cyclopropyl, cyclopentyl, cyclohexyl and the like. Cycloalkyl groups can be unsubstituted or substituted with one, two or three substituents independently selected from $C_{1-6}$ alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"$C_{1-6}$ alkyl" means straight or branched chain alkyl moieties containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylproply, n-hexyl and the like. Other numbers of carbon atoms indicated in this manner such as $C_{1-10}$ likewise represent straight or branched chain alkyls with the number of carbons indicated.

The indolyl moiety of Formula I may be substituted at

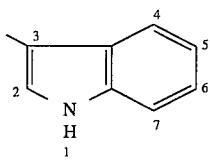

position 5 by H, Br, $CH_3$, or $OCH_3$, (represented in Formula I by $R_8$), and may be substituted at positions 4, 5, 6 or 7 by H or $CH_3$ (represented in Formula I by $R_7$). However, one of $R_7$ or $R_8$ must be hydrogen.

"Aryl" means monocyclic or bicyclic carbocyclic ring systems having one or more aromatic rings including, but not limited to, phenyl, naphthyl, tetrahydronaphthyl, indanyl and the like. Aryl groups can be substituted or unsubstituted with one, two or three substituents independently selected from $C_{1-6}$ alkyl, haloalkyl, alkoxy, thioalkoxy, aminoalkylamino, dialkylamino, hydroxy, halo, mercapto, nitro, carboxaldehyde, carboxy, carboalkoxy and carboxamide.

"Inner salt", also known as zwitterion, is a molecule which carries a positive and a negative charge, an example of which is Example 1 herein.

"Stereoisomer" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereoisomers). For amino-acids, the designations L/D, or R/S can be used as described in IUPAC-IUB Joint Commission on Biochemical Nomenclature, *Eur. J. Biochem.* 138:9–37 (1984).

"Pharmaceutically acceptable salts" means both acid addition salts and metal and amine salts which are known to be non-toxic and useful derivatives in the preparation of pharmaceutical formulations suitable for end-use applications.

Pharmaceutically acceptable acid addition salts include the known non-toxic organic or inorganic acid addition salts Of the base compounds of Formula I. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, and 2-phenoxybenzoic acids. Other organic acids which form suitable salts are the sulfonic acids such as methane sulfonic acid and 2-hydroxyethane sulfonic acid. Either the mono- or di-acid salts are prepared by standard techniques such as by dissolving the free base in an aqueous or aqueous-alcohol solution or other suitable solvent containing the appropriate acid and isolating by evaporating the solution, or by reacting the free base in an organic solvent in which case the salt separates directly or can be obtained by concentration of the solution. In general, the acid addition salts of the compounds of this invention are crystalline materials which are soluble in water and various hydrophilic forms, demonstrate higher melting points and an increased stability.

Pharmaceutically acceptable metal and amine salts are those salts which are stable under ambient conditions, and wherein the cation does not contribute significantly to the biological activity of the salt. Suitable metal salts include the sodium, potassium, calcium, barium, zinc, and aluminum salts. The sodium and potassium salts are preferred. Suitable amine salts are prepared from amines which have sufficient basicity to form a stable salt, and preferably include those amines which are frequently used in medicinal chemistry because of their low toxicity and acceptability for medical use. These include the trialkylamines such as triethylamine, and others including procaine, dibenzylamine, N-benzyl-betaphenethylamine, N-ethyl-piperidine, benzylamine, and dicyclohexylamine.

"Hydrate" is a molecule which has water in the form of $H_2O$ molecules associated therewith.

"To Treat" or "Treatment" of a disease or condition means to prevent or alleviate the patient's disease or condition.

"Patient" refers to a warm-blooded animal, such as for example rats, mice, dogs, cats, guinea pigs, primates and humans.

The compounds of this invention may be prepared by the application of analogous chemical reactions known in the art, using reactants which are already known or which may be prepared using standard processes and techniques known in the art. In its essence, the general method for preparing the compounds of Formula I my be depicted by the reaction Schemes that follow. In those schemes, the following terms have these meanings:

"L" means leaving group. Suitable leaving groups include triflates, alkyl or aryl sulfonates (e.g, $CF_3SO_2O$, tosylate, mesylate) and halides (Br, Cl or I.).

"Pg" means an appropriate protecting group. The term applies to protecting groups for atoms such as nitrogen or oxygen which are susceptible to undesirable chemical reactions. Appropriate protecting groups can be found, for example, in *Protective groups in Organic Synthesis, 2nd ed.*, Theodora W. Greene, John Wiley & Sons, Inc., New York 1991, incorporated herein by reference.

$R_1$, $R_2$, $R_3$, X, and Z have the meanings as previously defined. $R_1'$, $R_2'$, $R_3'$, and $R_4'$ are each protecting groups (Pg). It should be noted that Pg can be $R_1$, $R_2$ or $R_3$ except for hydrogen.

Scheme A

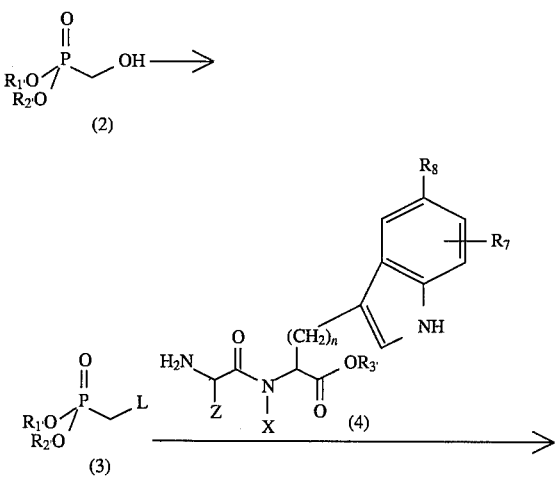

-continued
Scheme A
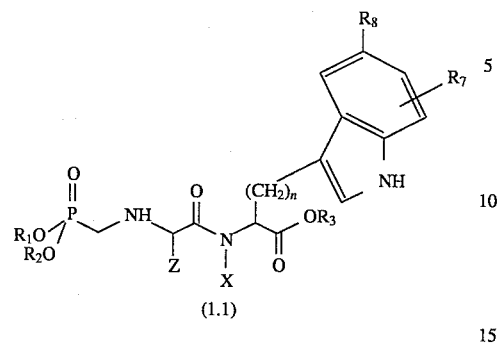
(1.1)
Scheme B:
alternative to scheme A
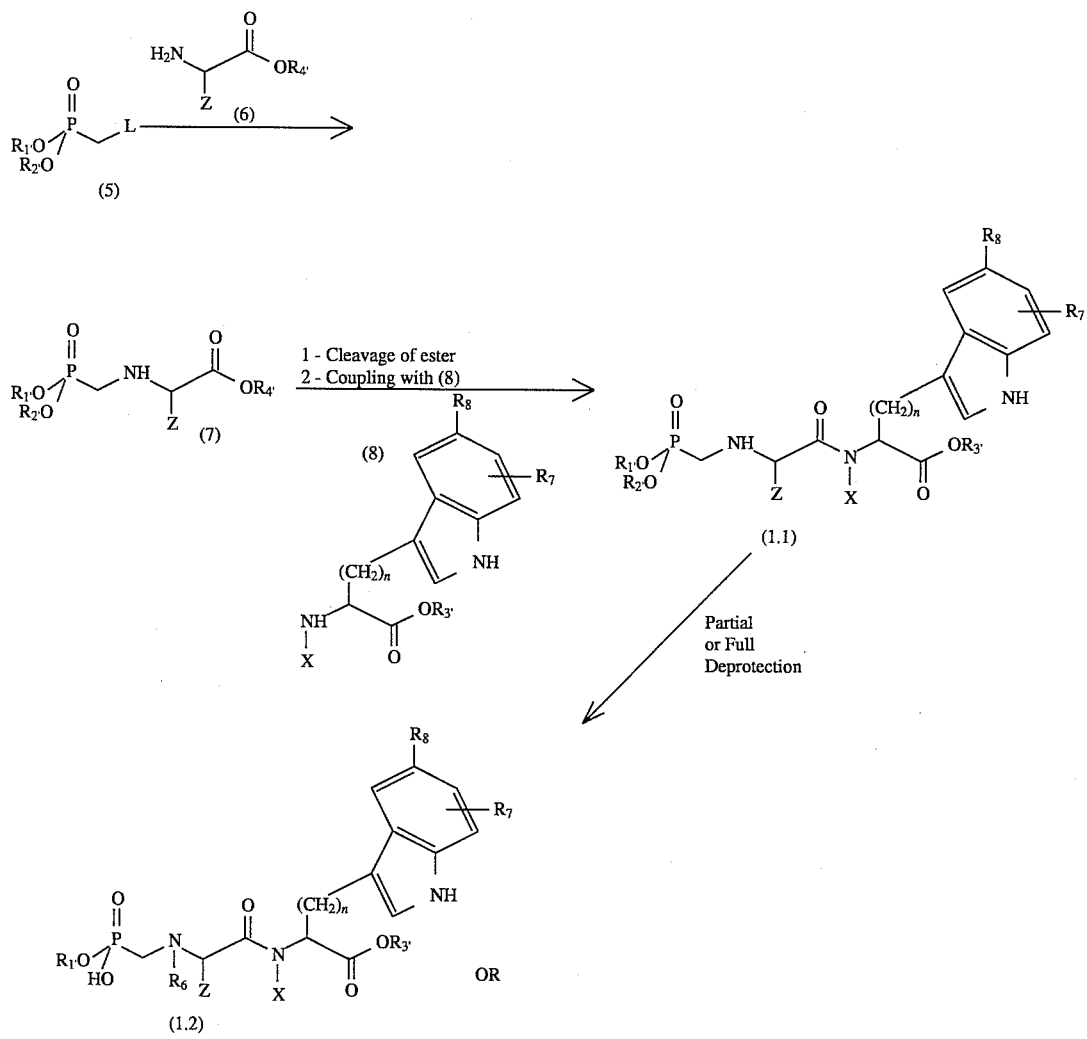

-continued
Scheme B:
alternative to scheme A

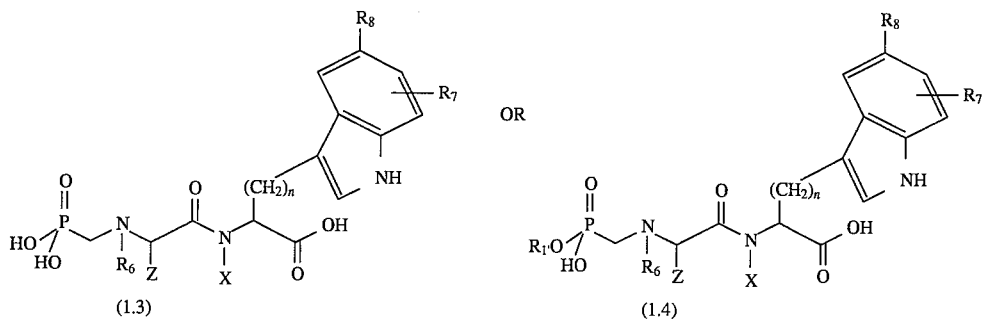

The dipeptide backbone was built using the well known strategy which consists of forming a peptide bond by coupling an aminoacid, with appropriate protecting group(s) such as tert-butyloxycarbonyl (BOC), with a peptide ester using a suitable coupling reagent. It includes the activation of carboxylate with dicyclohexylcarbodiimide (DCC) or, alternatively, according to the mixed anhydride method. Selective deprotection of the BOC to generate the free amine may be achieved using an etheral solution of hydrochloric acid, trifluoroacetic acid or formic acid. Examples of formation of the peptide bond can be found in, for example, *PEPTIDE CHEMISTRY, A PRACTICAL TEXTBOOK*, by Miklos Bodansky Springer-Verlag Berlin Heidelberg 1988, incorporated herein by reference. Starting materials are commercially available from, for example, Aldrich can supply dibenzylphosphite, diethylphosphite, dipropylphosphite and dibutylphosphite. Available from Bachem of Switzerland are the BOC-Leu; Leu-OMe, HCl; BOC-Phe-OH; BOC-HomoPhe-OH, BOC-D-Leu, $H_2O$; and Trp-OBz, HCl.

The dipeptides having an indolyl moiety wherein one of $R_7$ or $R_8$ is other than hydrogen may be prepared using amino acids obtained from Aldrich Chemical Co. of Milwaukee, Wis., (5-bromotryptophan, 5-methoxytryptophan or 5-methyltryptophan), Sigma Chemical Co. of the U.S.A. (4-methyltryptophan or 7-methyltryptophan), and Fluka Chemical Co. of Switzerland (6-methyltryptophan).

Referring to Scheme A, the introduction of the phosphonomethyl moiety utilized hydroxymethyl phosphonic esters (2) prepared by the method of A. Foucaud [*Synthesis* 916 (1982)]. The hydroxyl function is activated as a leaving group (L) (3), preferably as the trifluoromethyl sulfonate, and is substituted with the amino-terminal of a dipeptide (4) whose carboxy-terminal was protected, usually as ester shown as $R_3'$.

For example, hydroxymethyl phosphonic ester (2) is activated as the trifluoromethane sulfonate, by reaction with trifluoromethanesulfonic anhydride or trifluoromethanesulfonyl chloride at a low temperature ranging from −60° C. to 0° C. in an aprotic solvent, for example $CH_2Cl_2$, tetrahydrofuran, diethyl ether or dimethylformamide, or mixtures of these solvents. The protons are neutralized with a sterically hindered base, for example, 2,6-lutidine or with a metal hydride, for example, sodium hydride.

The dipeptide (4) is reacted with the activated phosphonoester (3) by adding a solution of (4) in an aprotic solvent at temperatures between 0° C. and 40° C. for a reaction time ranging from 1 hour to 3 days. A similar base for formation of trifluoromethylsulfonate is used. The yields may be improved by adding hexamethyl phosphoramide, dimethylformamide or the like.

As an alternative shown in Scheme B, it may be also convenient to react the protected intermediate (5) with an aminoacid ester (6) to produce the phosphonomethylaminoacid ester (7). The ester (7) is de-esterified and coupled with an amino ester (8) to produce a protected phosphonomethyldipeptide (1.1).

For example, the protected intermediate (5) is reacted with the aminoacid ester (6) under similar conditions as the reaction between (3) and (4) to produce the phosphonomethylaminoacid ester (7). The ester (7) is de-esterified using a base, sodium hydroxide, potassium hydroxide or lithium hydroxide in aqueous methanol, aqueous methoxyethanol or aqueous tetrahydrofuran at room temperature for one hour to twenty-four hours.

The amino ester (8) coupled with the de-esterified ester derived from (7) to produce the protected phosphonomethyl dipeptide (1.1) by activation of the carboxylate with dicyclohexylcarbodiimide, by forming a mixed anhydride (for example by using isobutylchloroformate) or by forming an acylazide using diphenylphosphoryl azide (DPPA). Depending on the nature of the so-formed activated ester, the reaction with the amino ester occurs between −20° C. and 40° C. The acylazide reacts from −10° C. to 10° C. Reaction time varies from one hour to three days.

The protected phosphono-methyldipeptide (1.1) can then be partially or fully deprotected. When all the protecting groups are benzyl, the fully deprotected compounds of Formula I (1.3) are conveniently obtained by hydrogenolysis under basic conditions in a biphasic system. Partial deprotection of the compounds of Formula I (1.2 or 1.4) may be achieved by hydrogenolysis, by action of diluted acid or base, or by reaction with trimethylsilyl halides.

The following gives specific examples of preferred compounds of the present invention and methods of making same. However, it is understood that the present invention is not to be limited by these exemplifications in any way and that other methods of making compounds known in the art may be employed.

EXAMPLE 1

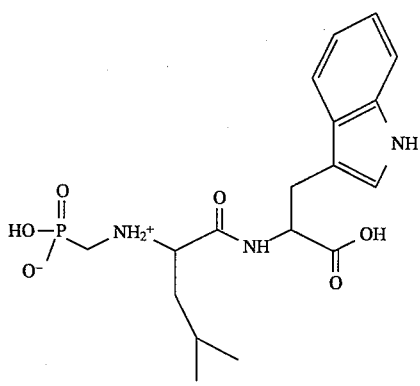

N-(N-Phosphonomethyl-L-leucyl)-L-tryptophan

Step A: N-(N-Dibenzyloxyphosphinylmethyl-L-leucyl)-L-tryptophan, benzyl ester

Dibenzyloxyphosphinylmethanol (372 mg) in anhydrous methylene chloride (5 ml) was added slowly to a methylene chloride solution (10 ml) of freshly distilled 2,6-lutidine (0.36 ml) and triflic anhydride (0.25 ml) cooled at −50° C. The mixture was stirred for 10 minutes at −50° C. and the temperature was allowed to warm to 0° C. for one hour.

Without isolation, to the so formed trifluoromethanesulfonic acid, dibenzyloxyphosphinylmethyl ester was then added at 0° C. L-leucyl-L-tryptophan, benzyl ester (500 mg) as the free amine in anhydrous methylene chloride (5 ml). The mixture was stirred for 1 hour at 0° C. and overnight at room temperature. Evaporation of the reaction mixture under vacuum gave an orange oil (1.60 g) which was purified by flash chromatography on silica gel (55 g, 230–400 Mesh). The title compound was eluted with a mixture of ethyl acetate and heptane in a ratio varying from 1/1 to 1/0. Evaporation of solvent yielded a colorless oil (240 mg). $^{31}$p NMR: CDCl$_3$ δ(relative to ext. H$_3$PO$_4$) multiplet (8 lines) (J=9 Hz) at 27.0 ppm.

Step B: N-(N-Phosphonomethyl-L-leucyl)-L-tryptophan

N-(N-Dibenzyloxyphosphinylmethyl-L-leucyl)-L-tryptophan, benzyl ester (240 mmg) and 10% palladium on charcoal (40 mg) in an heterogeneous mixture of ethyl acetate (10 ml) and aqueous solution (10 ml) of potassium hydrogenocarbonate (89 mg) were stirred at room temperature under hydrogen at normal pressure for 3 hours. The mixture was degased and the catalyst filtered off. The aqueous layer was separated, washed with ethyl acetate, filtered and lyophilized to afford a white powder (192 mg). This material was redissolved in water (10 ml) and neutralized by the slow addition of aqueous hydrochloric acid (N/10, 11 ml). The resulting precipitate was collected and dried under vacuum to afford the title compound as a white powder (115 mg).

$^{31}$p NMR: DMSO δ(relative to ext. H$_3$PO$_4$) multiplet at 14 ppm.

Anal. calculated for $C_{18}H_{26}N_3O_6P$, 1.2 H$_2$O

C: 49.93 H: 6.61 N: 9.70

Found C: 49.91 H: 6.53 N: 9.65

Melting point: endotherm at 232° C. by DSC.

EXAMPLE 2

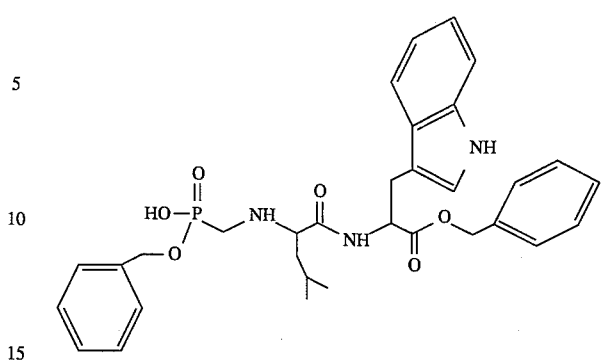

N-(N-Benzyloxyhydroxyphosphinylmethyl-L-leucyl)-L-tryptophan, benzyl ester

N-(N-Dibenzyloxyphosphinylmethyl-L-leucyl-L-tryptophan, benzyl ester (100 mg) (Example 1, Step A) dissolved in ethyl acetate (5 ml) was hydrogenated over palladium on charcoal (10%, 15 mg) under normal pressure at room temperature for 8 hours. The mixture was filtered and the so-obtained solid was extracted with methanol to afford after evaporation of solvent the title compound as a white solid (70 mg).

$^{31}$p NMR: CD$_3$OD δ(relative to ext. H$_3$PO$_4$) multiplet at 9.6 ppm.

Anal. calculated for $C_{23}H_{38}N_3O_6P$, 0.5 H$_2$O

C: 63.99 H: 6.54 N: 7.00

Found C: 64.06 H: 6.32 N: 6.98

EXAMPLE 3

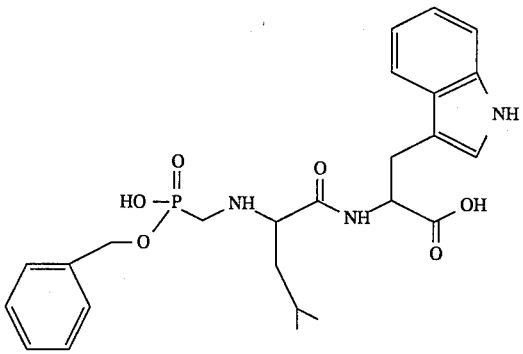

N-(N-Benzyloxyhydroxyphosphinylmethyl-L-leucyl)-L-tryptophan

A solution N-(N-(Dibenzyloxyphosphinylmethyl-L-leucyl)-L-tryptophan, benzyl ester (100 mg) (Example 1, Step A) in ethanol (5 ml) is treated with an aqueous solution of potassium hydroxyde 0.30 ml, 1N). Stirring is maintained for 4 days at room temperature. Upon completion of the reaction the mixture is evaporated under vacuum and the residue redissolved in water and is precipitated by addition of diluted hydrochloric acid allowing the recovery of the title compound.

EXAMPLE 4

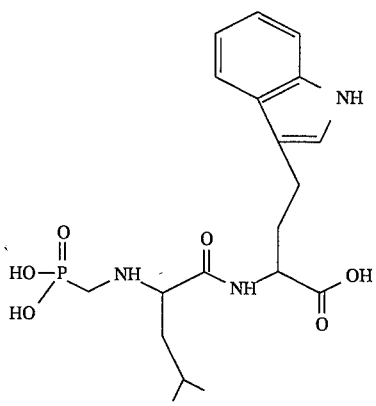

N-(N-Phosphonomethyl-L-leucyl)-DL-homotryptophan

Step A: L-Leucyl-DL-homotryptophan, ethyl ester

Ethyl 4-(β-indolyl)-2-ketobutyrate is dissolved in ethanol, then aqueous concentrated ammonia in excess and 10% Pd/C are added. The mixture is hydrogenated in a pressure apparatus at 5 bars. The catalyst is filtered and the filtrate evaporated in vacuo to yield a crude material which is coupled to N-tert-butyloxycarbonyl-leucine using dicyclohexylcarbodiimide with hydroxybenzotriazole in methylene chloride. Dicyclohexylurea is removed by filtration and the crude peptide obtained after evaporation of solvent is purified by chromatography on silica gel to afford N-(N-tert-butyloxycarbonyl-L-leucyl)-DL-homotryptophan, ethyl ester. Reaction with formic acid and extraction of the free base with aqueous sodium carbonate/ethyl acetate yields the title compound.

Step B: N-(N-Dibenzyloxyphosphinylmethyl-L-leucyl)-DL-homotryptophan, ethyl ester The title compound is obtained by an analogous procedure described for the preparation of N-(N-Dibenzyloxyphosphinylmethyl-L-leucyl)-L-tryptophan, benzyl ester (Example 1).

Step C: N-(N-Dibenzyloxyphosphinylmethyl-L-leucyl)-DL-homotryptophan

A solution of N-(N-Dibenzyloxyphosphinylmethyl-L-leucyl)-DL-homotryptophan, ethyl ester in 2-methoxyethanol is treated with an aqueous solution of lithium hydroxyde (1 equivalent, 2-methoxyethanol/water: 9/1 in Vol.). Evaporation of solvent and acidification give the title compound.

Step D: N-(N-Phosphonomethyl-L-leucyl)-DL-homotryptophan

The title compound is obtained by hydrogenation of N-(N-Dibenzyloxyphospinylmethyl-L-leucyl)-DL-homotryptophan following the procedure described for the preparation of N-(N-phosphonomethyl-L-leucyl)-L-tryptophan (Example 1).

EXAMPLE 5

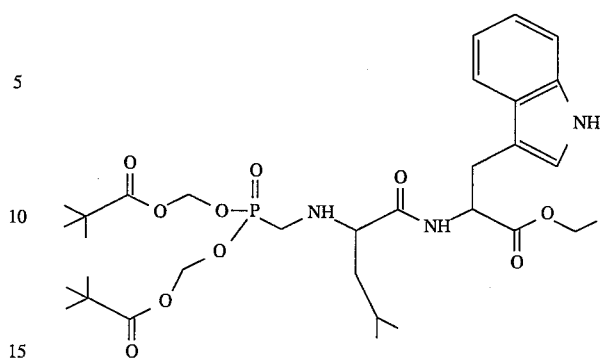

N-[N-(di-(pivaloyloxymethyl)-phosphonyl)-leucyl]-L-tryptophan, ethyl ester

Step A: N-(N-Phosphonomethyl-L-leucyl)-L-tryptophan, ethyl ester

A solution of N-(N-Dimethylphosphonomethyl-L-leucyl)-L-tryptophan, ethyl ester is treated with trimethylsilyl bromide in methylene chloride at room temperature. The mixture is concentrated and the residue is treated with water, filtered and dried to give the title compound.

Step B: N-[N-(di-(Pivaloyloxymethyl)-phosphonyl)-leucyl]-L-tryptophan, ethyl ester A solution of N-(N-Phosphonomethyl-L-leucyl)-L-tryptophan, ethyl ester and 18 crown-6 in toluene is cooled at 0° C. and is treated with potassium bis-trimethylsilylamide (2 equivalents). The mixture is reacted for 18 hours with iodomethylpivalate (2 equivalents). Ethyl acetate is added, the mixture is washed with water, dried, concentrated and chromatographed on silica gel to obtain the title compound.

EXAMPLE 6

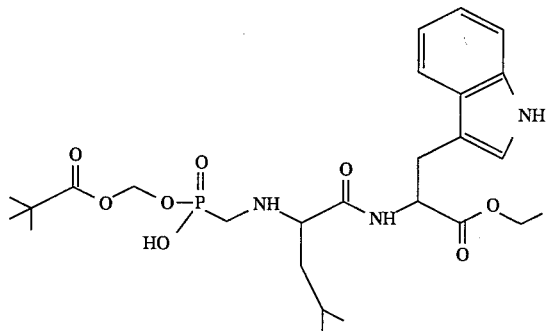

N-(N-Pivaloyloxymethyloxyhydroxyphosphinyl-L-leucyl)-L-tryptophan, ethyl ester

A solution of N-[N-(di-Pivaloyloxymethyl)-phosphonyl)leucyl]-L-tryptophan, ethyl ester in ethanol is cooled at 0° C. and sodium hydroxyde (1 equivalent) is added dropwise. Stirring is continued for 15 minutes and the reaction mixture is neutralized with 1N hydrochloric acid (1 equivalent). The mixture is concentrated under reduced pressure, the residue is partioned between methylene chloride and cold water. The organic layer is dried and concentrated under vacuum. The phosphonic acid monoester is finally purified by flash chromatography on silica gel.

EXAMPLE 7

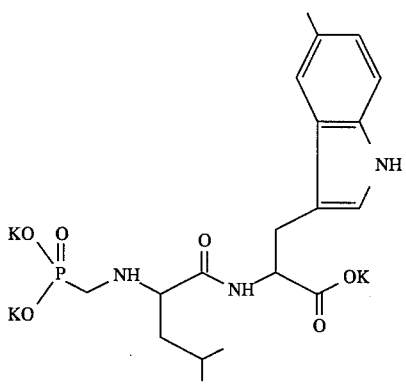

N-(N-Phosphonomethyl-L-leucyl)-DL-5-methyltryptophan, tripotassium salt

Step A: DL-5-Methyltryptophan, benzyl ester, hydrochloride

DL-5-methyltryptophan (2.03 g) dissolved in methanol was reacted with di-tert-butyl dicarbonate (2.17 g) and triethylamine (1.02 g) at room temperature for 4 hours. The reaction mixture was evaporated and extracted with ethyl acetate/water. Acidification at pH2 of the aqueous layer with diluted hydrochloric acid, extraction with ethyl acetate, drying over magnesium sulfate and solvent evaporation afforded N-(tert-butoxycarbonyl)-DL-5-methyltryptophan as a white solid.

The latter compound (2.72 g) solubilized in a mixture of methylene chloride and acetonitrile (1/1, 100 ml) was reacted at 0° C. with dicyclohexylcarbodiimide (1.80 g) and hydroxybenzotriazole, hydrate (1.31 g). The mixture was stirred ½ hour at 0° C. before the addition of benzyl alcohol (0.97 g) and 4-dimethylaminopyridine (96 mg). Stirring was maintained for one week at room temperature and the mixture was diluted with ethyl acetate and filtered. Extraction with ethyl acetate and 5% aqueous citric acid followed by washing of the organic layer with aqueous sodium bicarbonate and brine, drying over magnesium sulfate and solvent evaporation yielded a crude material which was purified on silica gel (230–400 Mesh, 90 g). Elution with ethyl acetate/heptane: ¼ allowed the recovery of N-tert-butoxycarbonyl)-DL-5-methyltryptophan, benzyl ester as a white solid (1.08 g). This material was suspended in formic acid and stirred for 5 hours at room temperature. The residue resulting of formic acid evaporation was taken up in a mixture of methanol and diluted hydrochloric acid and evaporated to yield the title compound as a white solid.

Step B: N-[N-(tert-Butoxycarbonyl)-L-leucyl]-DL-5-methyltryptophan, benzyl ester N-(tert-Butoxycarbonyl)-leucine, hydrate (249 mg) was coupled with D-L-5-methyltryptophan benzyl ester, hydrochloride (344 mg) using triethylamine (152 mg) as a base and dicyclohexylcarbodiimide (209 mg) as coupling reagent according to the procedure described in Example 13, Step A. A crude material was isolated as a white solid (472 mg) that was recrystallized in an ethyl acetate/heptane mixture (329 mg).

Step C: N-L-leucyl-DL-5-methyltryptophan

N-[N-(tert-Butoxycarbonyl)-L-leucyl]-DL-5-methyltryptophan, benzyl ester (321 mg) was cleaved in formic acid as previously described. The crude product was extracted with ethyl acetate and aqueous sodium carbonate. The organic layer was washed with brine and dried over sodium sulfate. Evaporation of the solvent yielded the title compound as an oil (241 mg).

Step D: N-[N-(Dibenzyloxyphosphinylmethyl)-L-leucyl]-DL-5methyltryptophan benzyl ester Dibenzyloxyphosphinylmethanol (171 mg) was coupled to N-L-leucyl-DL-5-methyltryptophan, benzyl ester (240 mg) as described in Example 1 to yield a yellow oil which was purified by chromatography on silica gel (85 g). Elution with ethyl acetate/heptane: 1/1 and pure ethyl acetate gave, after solvent evaporation, a yellow oil (136 mg). $^{31}$p NMR: CDCl$_3$ δ (relative to ext. H$_3$PO$_4$) multiplets at 26.9 and 26.7 ppm.

Step E: N-(N-Phosphonomethyl-L-leucyl)-DL-5-methyltryptophan, tripotassium salt

To N-[N-(dibenzyloxyphosphinylmethyl)-L-leucyl]-DL-5-methyltryptophan, benzyl ester (113 mg) dissolved in ethyl acetate (5 ml) was added a solution of potassium bicarbonate (41 mg) in water (5 ml) and 10% palladium on charcoal (30 mg). The mixture was stirred under hydrogen at atmospheric pressure and room temperature overnight. The mixture was filtered and lyophilized to afford the titled compound as a beige solid (81 mg).

$^{31}$p NMR: D$_2$O δ (relative to ext. H$_3$PO$_4$) multiplets at 12.2 and 9.8 ppm.

Analysis calculated for C$_{19}$H$_{25}$N$_3$O$_6$P3K, 2H$_2$O
C: 39.64 H: 5.08 N: 7.30
Found C:39.39 H: 5.30 N: 7.09.

EXAMPLE 8

In order to show the efficacy of the present compounds as antihypertensive agent, the following protocol may be used.

Male, Sprague-Dawley rats (250–300 g) are anaesthetized with urethane (1.25 g/kg, i.p.), supplemented as required. Tygon catheters are inserted into the right main carotid artery and the right femoral vein for arterial pressure monitoring and intravenous drug injections respectively. The preparation is allowed to stabilize for 30 minutes before starting the experimental protocol. Arterial pressure is monitored continuously with a TA2000 Gould stripchart recorder coupled to a data acquisition system (Dataflow from Crystal Biotech, U.S.A.).

Rats are randomized to be pretreated with an i.v. bolus injection (100 μl/100 g, flushed with 0.3 ml saline) of either saline or a dose (ranging from 1 to 100 μmol/kg) of phosphoramidon, or the compounds of the present invention. Five minutes later, Pro-ET1 (1 nmol/kg) is administered as an intravenous bolus injection (10 μl/100 g, flushed with 0.3 ml saline) and changes on arterial pressure are recorded for 30 minutes. To avoid any artefact, each rat receives only one pretreatment and only one dose of Pro-ET1. Pro-ET-1 elicits the hypertensive response, and phosphoramidon inhibits same. The compounds of the present invention are measured against the inhibition of phosphoramidon.

Human/porcine Pro-ET1 may be obtained from Peptide Institute (Osaka, Japan) and dissolved in 0.1% acetic acid to give $10^{-4}$M stock solutions, whose exact concentrations can be checked by absorbance spectrophotometry at 280 nm using an extinction coefficient of 7245M$^{-1}$cm$^{-1}$. The stock solutions are then aliquoted, lyophilized and stored at −20° C. The peptide is redissolved and diluted in saline on the day of the experiment.

EXAMPLE 9

In order to show the efficacy of the compounds of the present invention in the treatment of subarachnoid hemorrhage, the procedure used in *Life Sciences* 49:841–848 (1991) may be followed.

EXAMPLE 10

In order to show the efficacy of the compounds of the present invention in the treatment of asthma, Hartley guinea pigs of either sex are passively sensitized by intracardiac injection of antiserum prepared in rabbits (IgC) or guinea pigs (IgG or IgE) against a specific antigen (ovalbumin). The compounds are administered to the sensitized guinea pigs with route, dose, and time of compound administration dependent upon experimental design. The guinea pigs are challenged by aerosolization of the antigenic solution. The time to prostration following aerosolization and the incidence of mortality after five minutes are recorded. Negative controls consist of passively sensitized guinea pigs receiving no treatment and the incidence of lethality in this group is generally 90 to 100%. Chlorpheniramine and cyproheptadine may serve as positive controls.

EXAMPLE 11

In order to show the efficacy of the compounds of the present invention in the treatment of congestive heart failure, the procedure used in *Circulation* 82(6); 2226–2230 (1990) may be followed. This procedure is modified by pretreating the test animal with the compounds of the present invention.

EXAMPLE 12

In order to show the efficacy of the compound of the present invention in the treatment of renal failure, the procedure used in *European Journal of Pharmacology* 221: 77–83 (1992) may be followed.

EXAMPLE 13

In vitro Endothelin Converting Enzyme (ECE) assay via IP1 formation in rat brain slices. This assay measures the enzymatic activity responsible for the generation of functional ET-1 from pro-ET-1 by measuring the stimulation of phosphatidyl inositol turnover as a marker of ET-1 effect.

Rationale

It is well established that endothelin-1 (ET-1) can stimulate, in a dose-dependent manner, the turnover of the phosphatidyl inositol via the activation of ET receptors (Masaki et al., *Circulation*, 84:1457, 1991). The precursor of ET-1, i.e., proendothelin-1 (pro-ET-1) is unable to stimulate the phosphatidyl inositol turnover unless it is cleaved by a specific phosphoramidon sensitive protease, i.e., endothelin converting enzyme (ECE). Brain tissue is known to contain both the ET-1 receptors and the ECE (Gulati and Srimal, *Drug Devel. Res.*, 26:361, 1992). For this assay, an adaptation of the procedure of Brown et al., *J. Neurochem.*, 42:1379, 1984, was used.

Procedure

Peptides Preparation

Human/porcine ET-1 and pro-ET-1 were purchased from Peptide Institute (Osaka, Japan) and dissolved in 0.1% acetic acid solution to give a $10^{-4}$ M stock solution. The exact concentration of these solutions was checked by absorbance spectrophotometry at 280-nm, using the equation $C=A/L \epsilon_{280}$ [with C. the concentration of the peptide in solution, A the absorbance measured, L the optical path length of the solution and $\epsilon 280$ the extinction coefficient of the peptide in solution (8370 and 7025 $M^{-1}cm^{-1}$ for pro-ET-1 and ET-1, respectively)]. The stock solutions were then aliquoted, lyophilized and stored at −20° C. The peptides were redissolved and diluted in water on the day of the experiment (peptides for other tests also prepared by this methods).

Tissue Preparation

Male Sprague Dawley rats (Charles River, France), 200–300 g, were stunned, decapitated and the brain quickly removed onto a glass plate. The striatum were quickly dissected free of surrounding tissue and laid on the plastic disk of a McIlwain chopper. To prepare transverse slices, the tissues were cut into 0.35 mm thick slices, rotated 90° and cut a second time. The slices were suspended in physiological buffer (in mM: NaCl 118, KCl 5.0, $CaCl_2$ 1.3, $KH_2PO_4$ 1.0, $MgSO_4$ 1.2, $NaHCO_3$ 2, glucose 10, continuously gassed with carbogen) and used in assays for pro-ETs- and ETs-induced formation of inositol phosphates.

Stimulation of Phosphatidyl Inositol Turnover by pro-ET-1

Brain slices from 6 rats were suspended in buffer continuously gassed with carbogen. During the 60 minute preincubation period, the slices were in a container set in a shaking bath at 37° C. and gently agitated to keep them from settling. The buffer was changed every 15 minutes. During this time, 500 µl resin (see below) were placed in a small column and rinsed with water until the effluent pH was neutral. The appropriate volume of [$^3$H]-myo-inositol was mixed with a small volume of water and passed through the column. The resin was then rinsed with a quantity of water sufficient to obtain a total eluted volume of [$^3$H]-myo-inositol at the desired concentration.

Individual slices were distributed to flat-bottomed 5 ml vials containing 5 mM lithium chloride. An aliquot of purified [$^3$H]-myo-inositol was added to each vial to a final concentration of 0.1 µM and the tissues incubated for 30 minutes at 37° C. in a shaking bath. Antagonists were added, to reach the final concentration of $10^{-5}$M, in the appropriate vials, 15 minutes before addition of $10^{-6}$M pro-ET-1; equal volumes of buffer/solvent were added to the control vials. After each addition, the vials were gently vortexed, flushed with carbogen, capped and returned to the shaking bath at 37° C. The reactions were stopped after 30 minutes incubation with pro-ET-1 by addition of 940 µl chloroform/methanol (1:2, v/v) and the samples were vigorously vortexed. Additional chloroform and water (310 µl each) were added to each vial and the phases separated by centrifugation. An aliquot of 750 µl of the aqueous phase was taken to quantify the formation of [$^3$H]-myo-inositol monophosphates ([$^3$H]-IP1).

In these conditions the stimulation of phosphatidyl inositol turnover by pro-ET-1 can be assessed by measuring the amount of accumulated [$^3$H]-IP1.

[$^3$H]-IP1 was separated from [$^3$H]-myo-inositol by anion exchange chromatography. One hundred BioRad Econocolumn chromatography columns (0.7×15 cm) were set up in a perspex holder so that each column could be eluted directly into a rack of 20 ml scintillation counting vials. Each column contained 1 ml of a 50% suspension of AG 1-X8 resin, 100–200 mesh, formate form. Elution buffers were delivered using a peristaltic pump set up to wash 20 columns at a time. Before the addition of the aqueous phase, the resin in the columns was washed 3 times with 10 ml of 10 mM trisformate, pH 7.4. After adding the aqueous phase, each column was washed twice with 10 ml of distilled water followed by 10 ml of 60 mM ammonium formate with 5 mM sodium tetraborate; the eluants were discarded. IP1 was eluted into scintillation vials with 8 ml of 0.2M ammonium formate in 0.1M formic acid. Subsequently, the resin was regenerated by washing with 10 ml 1M ammonium formate in 0.1M formic acid followed by 3 times 10 ml of 2M formic acid. The columns were stoppered and filled with 2M formic acid. The tritium eluted from the columns was quantitated using liquid scintillation counting (dpm).

The AG 1-X8 resin was batch-washed before use as described by Kakamoto and Armstrong, *J. Biol. Chem.,* 237:208, 1962. In this wash procedure, formic acid was substituted for HCl and, after the acetone wash, the resin was dried for a few minutes and then resuspended in 1M formic acid, 1:1, weight/volume and stored at 4° C.

Analysis of Results

In each experiment, measurements were realized in triplicate.

Blank (no tissue) and basal (non-stimulated) values were determined and subtracted from all the IP1 changes measured. In order to standardize observations, the activity of 25 µl of [$^3$H]-myo-inositol (IM, in dpm) was estimated for each experiment and the IP1 changes measured were multiplied by the factor $10^6$/IM. The final data were then expressed as mean % (of at least 3 observations) of the maximal response induced by pro-ET-1 $10^{-6}$M in the absence of inhibitor.

When a compound, at $10^{-5}$M induced more that 50% inhibition of pro-ET-1-mediated effect, a complete dose-response curve was then constructed with this inhibitor, its $IC_{50}$ (concentration inhibiting 50% of the effect of pro-ET1 $10^{-6}$M) determined graphically. In that case, it is also important to know the influence of such a compound on the effect of ET1, and a dose-response curve of the compound was constructed against ET1 $10^{-6}$M, using the same experimental procedure described for pro-ET-1. The concentration reducing 50% of the effect of ET1 $10^{-6}$M ($RC_{50}$) was then determined graphically.

When a compound, at the dose of $3 \times 10^{-5}$M, did not reduce by more than 50% the effects of pro-ET-1 or ET-1, this compound was characterized with an $IC_{50}$, or $RC_{50}$, >30 µM and the % of maximal reduction observed was recorded.

For example, for phosphoramidon (reference compound) $IC_{50}=6.4\pm1.1$ µM and $RC_{50}>30$ µM with 75±9% maximal reduction.

For pharmacological end-use applications, the compounds of Formula I are preferentially administered in the form of their pharmaceutically acceptable acid addition salts. Of course, the effective dosage of the compounds will vary according to the indication for use, individual potency of each compound employed, the severity and nature of the disease being treated and the particular subject being treated. In general, effective results can be achieved by administering a compound at a dosage of about 0.01 mg to about 20 mg per kilogram of body weight per day, administered systemically. Therapy should be initiated at lower dosages. The dosage thereafter may be administered orally in solid dosage forms, e.g., capsules, tablets, or powders, or in liquid forms, e.g., solutions or suspensions. The compounds may also be injected parenterally in the form of sterile solutions or suspensions.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula I compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, dissintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula I compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The compounds of the present invention may be incorporated into an aerosol preparation by means commonly known to those skilled in the art. The aerosol preparation may be prepared for use as a topical aerosol or may be prepared for inhalation. The aerosol preparation may be in the form of a solution or suspension and may contain other ingredients such as solvents, propellants and/or dispersing agents. Typical examples of aerosol preparations are shown in *Remington's Pharmaceutical Sciences* 18th ed., Mack Publishing Company, Easton Pa., pp. 1694–1712 (1990).

As is true for most classes of compounds suitable for use as therapeutic agents, certain subgeneric groups and certain specific compounds are preferred. In this instance those compounds which are preferred have $R_1$ as H, $R_2$ as nothing and $R_6$ as $H_2$, $R_3$ as H or $(CH_2)$ aryl, Z as iso-butyl, and n as 1.

What is claimed is:

1. A compound having the formula of:

$$R_1O-\underset{\underset{R_2O}{|}}{\overset{\overset{O}{\|}}{P}}-CH_2-\underset{\underset{R_6}{|}}{\overset{\overset{Z}{|}}{N}}-\underset{\underset{O}{\|}}{C}-\underset{\underset{(CH_2)_n}{|}}{\overset{\overset{X}{|}}{N}}-\overset{\overset{O}{\|}}{C}-OR_3 \qquad \text{Formula I}$$

(with indole bearing $R_7$, $R_8$ substituents and NH)

stereoisomers, hydrates, inner salts or pharmaceutically acceptable salts thereof,
wherein $R_1$ or $R_2$ are each independently a hydrogen, $C_{1-6}$ alkyl, $(CH_2)_m$-aryl, $R_4$—C(O)O—CH($R_5$)— or nothing when the inner salt is formed, provided that when one of $R_1$ or $R_2$ is a hydrogen, $C_{1-6}$ alkyl, or $(CH_2)_m$—aryl, then the other is hydrogen or nothing when the inner salt is formed;

$R_3$ is hydrogen, $C_{1-6}$ alkyl, $(CH_2)_m$-cycloalkyl or $(CH_2)_m$-aryl;

$R_4$ is $C_{1-10}$ alkyl, $(CH_2)_m$-cycloalkyl or $(CH_2)_m$-aryl;

$R_5$ is $C_{1-6}$ alkyl, $(CH_2)_m$-cycloalkyl or hydrogen;

$R_6$ is H, or $H_2$ when one of $R_1$ or $R_2$ is nothing thus forming the inner salt;

$R_7$ is $CH_3$ or H;

$R_8$ is H, Br, $CH_3$, or $OCH_3$, provided that one of $R_7$ or $R_8$ are H;

Z is $(CH_2)_m$-aryl or $C_{1-12}$ alkyl;

X is hydrogen or $C_{1-6}$ alkyl;

each m is independently 0, 1, 2 or 3; and n is 1, 2 or 3.

2. The compound of claim 1 wherein $R_1$ is H.

3. The compound of claim 1 wherein $R_2$ is nothing and $R_6$ is $H_2$.

4. The compound of claim 1 wherein $R_3$ is H or $(CH_2)$-aryl.

5. The compound of claim 1 wherein Z is iso-butyl.

6. The compound of claim 1 wherein X is H.

7. The compound of claim 1 wherein the compound is N-(N-Phosphonomethyl-L-leucyl)-L-tryptophan.

8. A pharmaceutical composition comprising the compound of claim 1 with a pharmaceutically acceptable carrier.

9. The compound of claim 1 wherein the compound is N-(N-Benzyloxyhydroxyphosphinylmethyl-L-leucyl)-L-tryptophan, benzyl ester.

10. The compound of claim 1 wherein the compound is N-(N-Benzyloxyhydroxyphosphinylmethyl-L-leucyl)-L-tryptophan.

11. The compound of claim 1 wherein the compound is N-(N-phosphonomethyl-L-leucyl)-DL-homotryptophan.

12. The compound of claim 1 wherein the compound is N-[N-(di-(Pivaloyloxymethyl)-phosphonyl)-leucyl]-L-tryptophan, ethyl ester.

13. The compound of claim 1 wherein the compound is N-(N-Pivaloyloxymethyloxyhydroxyphosphinyl-L-leucyl)-L-tryptophan, ethyl ester.

14. A method of inhibiting Endothelium Converting Enzyme in a patient in need of such therapy comprising administering to the patient a sufficient amount of a compound of claim 1.

15. A method of making a compound of formula I:

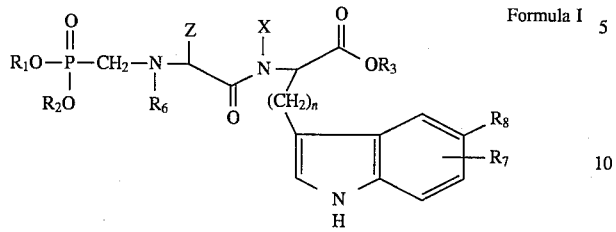

stereoisomers, hydrates, inner salts or pharmaceutically acceptable salts thereof,
wherein $R_1$ or $R_2$ are each independently a hydrogen, $C_{1-6}$ alkyl, $(CH_2)_m$-aryl, $R_4$—C(O)O—CH($R_5$)- or nothing when the inner salt is formed, provided that when one of $R_1$ or $R_2$ is a hydrogen, $C_{1-6}$ alkyl, or $(CH_2)_m$-aryl, then the other is hydrogen or nothing when the inner salt is formed;

$R_3$ is hydrogen, $C_{1-6}$ alkyl, $(CH_2)_m$-cycloalkyl or $(CH_2)_m$-aryl;

$R_4$ is $C_{1-10}$ alkyl, $(CH_2)_m$-cycloalkyl or $(CH_2)_m$-aryl;

$R_5$ is $C_{1-6}$ alkyl, $(CH_2)_m$-cycloalkyl or hydrogen;

$R_6$ is H, or $H_2$ when one of $R_1$ or $R_2$ is nothing thus forming the inner salt;

$R_7$ is $CH_3$ or H;

$R_8$ is H, Br, $CH_3$, or $OCH_3$, provided that one of $R_7$ or $R_8$ are H;

Z is $(CH_2)_m$-aryl or $C_{1-12}$ alkyl;

X is hydrogen or $C_{1-6}$ alkyl;

each m is independently 0, 1, 2 or 3; and n is 1, 2 or 3.
comprising the steps of:

substituting the leaving group (L) of the phosphonic compound (3)

with the dipeptide (4)

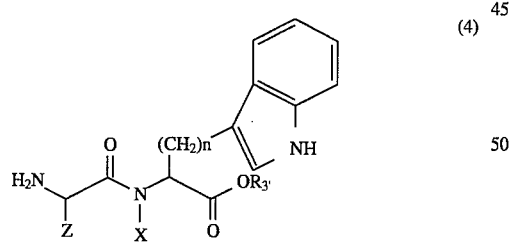

wherein $R_1'$ and $R_2'$ are each $C_{1-6}$ alkyl, $(CH_2)_m$-aryl, $R_4$—C(O)O—CH($R_5$)—, or other suitable protecting group if subsequently deprotected, and $R_3'$ is $C_{1-6}$ alkyl, $(CH_2)_m$-cycloalkyl, $(CH_2)_m$-aryl or any other suitable protecting group if subsequently deprotected, to produce dipeptide (1.1),

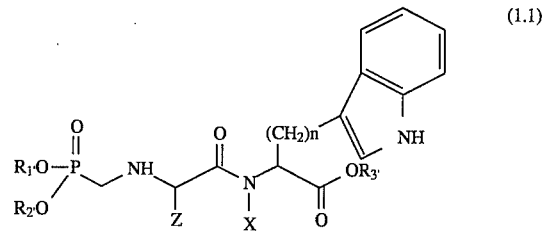

and optionally deprotecting at any of $R_1'$, $R_2'$ or $R_3'$ so that $R_1'=R_1$, $R_2'=R_2$, and $R_3'=R_3$, wherein Z, X and n have the previously described meanings;

or alternatively, de-esterifying ester (7) in the presence of a base wherein Z, $R_1'$ and $R_2'$ are as previously defined and $R_4'$ is any suitable protecting group,

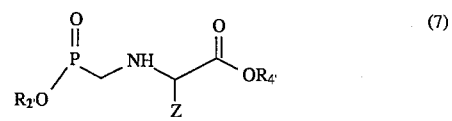

and coupling with amino ester (8) wherein $R_3'$, X and n are as previously defined

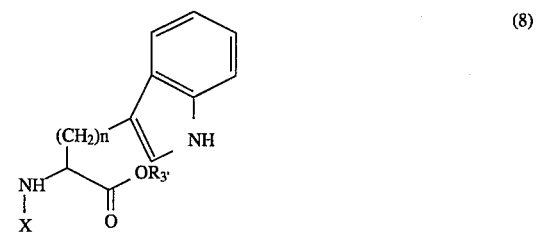

to produce the protected phosphonomethyl dipeptide (1.1)

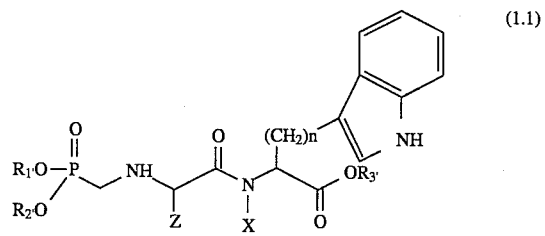

and optionally deprotecting at any of $R_1'$, $R_2'$ and $R_3'$, so that $R_1'=R_1$, $R_2'=R_2$, and $R_3=R_3$.

* * * * *

UNITED STATES PATENT AND TRADEMARK OFFICE
CERTIFICATE OF CORRECTION

PATENT NO. : 5,608,078　　　　　　　　　　　　　　　　Page 1 of 2

DATED : 04 March 1997

INVENTOR(S) : Hugues de'Orchymont, et al.

It is certified that error appears in the above-identified patent and that said Letters Patent is hereby corrected as shown below:

Title Page, Title Line of patent reads "PHOSPHONOMETHYLDIPEPTIDES AND PROCESS FOR PREPARATION THEREOF" - and should read --- PHOSPHONOMETHYLDIPEPTIDES .

Column 1, Line 1 of patent reads "PHOSPHONOMETHYLDIPEPTIDES AND PROCESS FOR PREPARATION THEREOF" - and should read ---PHOSPHONOMETHYLDIPEPTIDES.

Column 3, Line 40 of patent reads "Of" - and should read --- of .

Column 4, Line 25 of patent reads "my" – and should read --- may.

Column 14, Line 5 of patent reads "DL-5methyltryptophan" – and should read --- DL-5-methyltryptophan --

Column 16, Line 5 of patent reads "this methods" – and should read --- this method .

Column 18, Line 29 of patent reads "use oral" – and should read --- use in oral.

UNITED STATES PATENT AND TRADEMARK OFFICE
CERTIFICATE OF CORRECTION

PATENT NO. : 5,608,078

DATED : 04 March 1997

INVENTOR(S) : Hugues de'Orchymont, et al.

It is certified that error appears in the above-identified patent and that said Letters Patent is hereby corrected as shown below:

Column 22, Line 25 (Claim 15) of patent reads

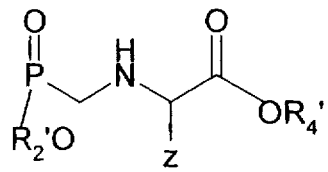

- and should read ---

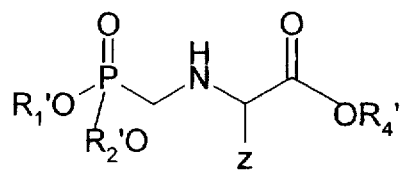

Signed and Sealed this

First Day of February, 2000

Attest:

Q. TODD DICKINSON

*Attesting Officer*   *Acting Commissioner of Patents and Trademarks*